United States Patent
Abebe (10) Patent No.: US 12,287,326 B2
(45) Date of Patent: Apr. 29, 2025

(54) FLUORESCENT TURN-ON CHEMOSENSORS FOR DETECTION OF ALUMINUM ION AND AZIDE

(71) Applicant: Morgan State University, Baltimore, MD (US)

(72) Inventor: Fasil Abebe, Elkrdige, MD (US)

(73) Assignee: Morgan State University, Baltimore, MD (US)

( * ) Notice: Subject to any disclaimer, the term of this patent is extended or adjusted under 35 U.S.C. 154(b) by 0 days.

(21) Appl. No.: 18/299,710

(22) Filed: Apr. 12, 2023

(65) Prior Publication Data

US 2023/0251246 A1  Aug. 10, 2023

Related U.S. Application Data (63) Continuation of application No. 16/987,688, filed on Aug. 7, 2020, now abandoned.

(60) Provisional application No. 62/883,785, filed on Aug. 7, 2019.

(51) Int. Cl.

| | | |
|---|---|---|
| C07D 311/00 | (2006.01) | |
| C07D 311/88 | (2006.01) | |
| C07D 491/107 | (2006.01) | |
| C07F 5/06 | (2006.01) | |
| G01N 21/78 | (2006.01) | |
| G01N 33/52 | (2006.01) | |

(52) U.S. Cl.
CPC .......... *G01N 33/52* (2013.01); *C07D 311/88* (2013.01); *C07D 491/107* (2013.01); *C07F 5/069* (2013.01); *G01N 21/78* (2013.01)

(58) Field of Classification Search
CPC ............................. G01N 33/52; C07D 311/88
USPC ................................................ 436/74; 544/1
See application file for complete search history.

(56) References Cited

PUBLICATIONS

Sen et al. "Al3+-Ion-Triggered Conformational Isomerization of a Rhodamine B Derivative Evidenced by a Fluorescence Signal-A Crystallographic Proof" Eur. J. Inorg. Chem. 2015, 1383-1389 (Year: 2015).*

(Continued)

*Primary Examiner* — Christine T Mui
*Assistant Examiner* — Emily R. Berkeley
(74) *Attorney, Agent, or Firm* — Whiteford, Taylor & Preston, LLP; Peter J. Davis (57) ABSTRACT

Two rhodamine reversible fluorescent sensor derivatives, $L_1$ and $L_2$, bearing 2-methoxy-1-naphthaldehyde and 5-bromo-3-methoxy salicylaldehyde units were synthesized using microwave-assisted organic synthesis and used for selective and sensitive reversible sequential fluorescence detection of aluminum ion ($Al^{3+}$) and azide ($N^{3-}$) in aqueous acetonitrile solution via the fluorescence spectral changes. Stoichiometry and binding mechanisms for both sensors are well characterized and established by the respective spectroscopic techniques. $L^1$ and $L^2$ sensors are useful for the analysis of $Al^{3+}$ and $N^{3-}$ in environmental samples and biological studies.

2 Claims, 10 Drawing Sheets

(56) References Cited

PUBLICATIONS

Abebe et al."Microwave-assisted synthesis of rhodamine derivatives" Green Chemistry Letters and Reviews 2018, vol. 11, No. 3, 237-245 (Year: 2018).*

Perkins et al."(E)-30,60-bis(Diethylamine)-2-[(2-methoxynaphthalen-1-yl)methyleneamino]spiro[isoindoline-1,90-xanthen]-3-one" Molbank 2017, 2017, M955 (Year: 2017).*

* cited by examiner

FLUORESCENT TURN-ON CHEMOSENSORS FOR DETECTION OF ALUMINUM ION AND AZIDE

BACKGROUND OF THE INVENTION

Field of the Invention

The present invention relates to rhodamine Schiff base compounds for the detection of micromolar levels of $Al^{3+}$ ions and azide ($N_3^-$).

Description of the Background

Several approaches discuss detection of aluminum but not in conjunction with azide. U.S. Pat. No. 9,891,237 relies on a Schiff base for metal cation detection, but its sensor relies on a form of benzazole. U.S. Pat. No. 7,615,377 also uses ligands for detection of metal ions, and it also is based on fluorescence, but it does not apply the specific formula towards the same specific ligands. U.S. Pat. No. 7,906,320 covers a fluorescence-based biosensor that can specifically detect metals and also discusses quenchers that emit at specific wavelength ranges. U.S. Pat. No. 7,018,840 refers to fluorescent metal sensors, with rhodamine complexed with metal ions through ligand binding but does not list aluminum as one of the exemplary metal ions. U.S. Pat. No. 5,567,619 detects for aluminum, among other elements/compounds and does mention some other similar attributes, such as chelation and certain color indications, but it is overall more primitive in nature.

SUMMARY OF THE INVENTION

The present invention relates to sensor compounds ("sensors") that are developed from rhodamine derivatives that may be used for detecting the presence of $Al^{3+}$ and other metals.

Widespread use of aluminum in pharmaceuticals, cooking utensils, aluminum foil, vessels, and trays can result in the moderate increase in $Al^{3+}$ concentration in food, and potentially damage the central nervous system in humans.

Novel and unobvious rhodamine Schiff base sensors $L_1$ and $L_2$ are described herein that are able to detect micromolar levels of $Al^{3+}$ ions by the chelation-enhanced fluorescence (CHEF) process. Also of note, $Al^{3+}$ complexes $L_1$-$Al^{3+}$ and $L_2$-$Al^{3+}$ behave as highly selective chemosensors for $N_3^-$ ions by quenching of the fluorescence in acetonitrile/water ($CH_3CN/H_2O$) medium at 25° C.

The rhodamine derivative sensors $L_1$ and $L_2$ bearing 2-methoxy-1-naphthaldehyde and 5-bromo-3-methoxy salicylaldehyde units were designed and synthesized from the parent rhodamine B and aromatic aldehydes in a two-step Schiff base condensation, using microwave-assisted organic synthesis (MAOS) and utilized towards sequential fluorescence detection of aluminum ion ($Al^{3+}$) and azide ($N_3^-$) in aqueous acetonitrile solution. Aluminum ion ($Al^{3+}$) triggers the formation of highly fluorescent ring-open spirolactam.

A mixture of ethanol with compound 2 and 2-methoxy-1-naphthaldehyde or with compound 2 and 5-bromo-3-methoxy salicylaldehyde was placed in a reaction vial and then stirred before being placed in a biotage microwave reactor. The closed reaction vessel in both cases was run under pressure and irradiated for 10 minutes. After cooling to room temperature, the resulting solid was filtered and washed three times with cold ethanol. After drying, the resulting sensor yield was measured—the $L_1$ sensor yielded 92%, while the $L_2$ sensor yielded 88%.

Absorption spectra studies showed that on incremental addition of $Al^{3+}$ ions, the absorption intensity at 315 nm increased gradually and a new absorption peak at 565 nm with a shoulder at 525 nm was generated by ring opening with a visual color change from colorless to pink. The well-defined isosbestic points at 340 and 375 nm clearly indicates the formation of a new complex species between $L_1$ and $Al^{3+}$. Absorption spectra of sensors recorded with the continuous addition of $Al^{3+}$ showed a continuous increase in the absorption at 565 nm and that was employed to calculate binding constants for $L_1$ and $L_2$ with $Al^{3+}$ using the Benesi-Hildebrand method.

The plot of absorbance of $L_1$ at 565 nm as a function of mole fraction of added $Al^{3+}$ metal ion reveals that these probes bind to the metal ion in 1:1 stoichiometry. The fluorescence spectrum of sensors $L_1$ and $L_2$ showed a peak at 585 nm upon the addition of $Al^{3+}$ corresponding to the delocalization in the xanthenes moiety of rhodamine.

The fluorescence and colorimetric response of the $L_1$-$Al^{3+}$ and $L_2$-$Al^{3+}$ complexes were quenched by the addition of $N_3^-$, which extracted the $Al^{3+}$ from the complexes and turned off the sensors, confirming that the recognition process is reversible. The recognition ability of the sensors was confirmed by fluorescence titration, Job's plot, 1H-NMR spectroscopy and density functional theory (DFT) calculations.

When $L_1$-$Al^{3+}$ is used as the sensor for $N_3^-$, high concentration of CN-interference must be eliminated by using mesoporous carbon based adsorbent. The addition of $N_3^-$ to the $L_1$-$Al^{3+}$ solution led to a change in color of the solutions from pink to colorless, which was observed with the naked eye. The addition of $N_3^-$ to the solution containing $L_1$-$Al^{3+}$ complex resulted in the reversal of the $Al^{3+}$ induced changes in the emission band at 585 nm in the fluorescence emission spectra.

Gradual addition of $N_3^-$ results in continuous decrease in the emission intensity at 585 nm. Based on fluorescence data, the detection limit of $L_1$-$Al^{3+}$ or $N_3^-$ was calculated as 12 μM. A similar finding was observed for complex $L_2$-$Al^{3+}$ towards $N_3^-$ ions. The $L_2$-$Al^{3+}$ system revealed remarkably selective fluorescence "off" behavior exclusively with $N_3^-$. The limit of detection value for $N_3^-$ ions was found at 18 μM. These results show that $L_1$-$Al^{3+}$ and $L_2$-$Al^{3+}$ binds $N_3^-$ ions with higher selectivity and the process is reversible.

Accordingly, there is provided according to an embodiment of the invention, a compound having the formula:

or

-continued

L₂

There is further provided according to the invention a compound having the formula:

L₁-Al³⁺ salt or

L₂-Al³⁺

There is further provided according to the invention a method for synthesizing the compound L₁, comprising mixing a compound having the formula

2 with 2-methoxy-1-naphthaldehyde and ethanol, stirring a resulting mixture until homogenous, and irradiating the resulting mixture in a microwave reactor.

There is further provided according to the invention a method for synthesizing the compound method for synthesizing the compound L2, comprising mixing a compound having the formula

2 with 5-bromo-3methoxy salicylaldehyde and ethanol, stirring a resulting mixture until homogenous, and irradiating the resulting mixture in a microwave reactor.

There is further provided according to the invention a method for determining a presence of Al³⁺ in a sample, comprising: contacting the sample with a colorless solution comprising compound $L_1$ or $L_2$ and observing whether the colorless solution turns pink in color, where a change in color of the solution to pink indicates the presence of Al³⁺ in the sample. According to a further embodiment of the invention, the colorless solution shows no absorption above 450 nm in UV-vis absorption spectra, and an absorption peak above 525 nm indicates the presence of Al³⁺ in the sample.

There is further provided according to the invention a method for determining a presence of $N_3^-$ in a sample, comprising: contacting the sample with a pink solution comprising a compound having the formula L₁-Al³⁺ salt or -continued $L_2$-$Al^{3+}$ and observing whether the pink solution turns colorless, where a change in color of the solution from pink to colorless indicates the presence of $N_3^-$ in the sample. According to a further embodiment of the invention, the pink solution shows an absorption peak above 525 nm in UV-vis absorption spectra, and no absorption above 450 nm indicates the presence of $N_3^-$ in the sample.

DETAILED DESCRIPTION

Chemicals and Instruments

All reagents and solvents were purchased as analytical-grade and used without further purification unless otherwise stated. Stock solutions of metal ions were prepared from their nitrate and chloride salts and anion species from their tetrabutylammonium salts. Distilled deionized water was used throughout the experiments. $^1$H-NMR and 13C-NMR spectra were recorded using an Avance 400 MHz spectrometer (BRUKER® Billerica, Karlsruhe, Germany) with tetramethylsilane (TMS) as internal standard and deuterated chloroform ($CDCl_3$) as solvent. NMR spectra were analyzed using MestReNova software (version 10, Mestrela Research, Feliciano Barrera-Bajo, Spain). The IR spectrum was obtained using FT-IR spectrometer (Shimadzu, IRAffinity-1S, Columbia, MD, USA). High resolution electrospray ionization mass spectrometry (ESI-MS) was acquired with a BRUKER® Apex-Qe instrument. All UV-vis spectroscopy experiments were recorded using a Cary UV/vis spectrophotometer 5000 (VARIAN®, Walnut Creek, CA, USA). Fluorescence emission spectra experiments were measured using a Cary 60 series spectrometer (AGILENT® Walnut Creek, CA, USA), with excitation and emission slit widths of 5 nm and excitation wavelength at 510 nm. MAOS reactions were carried out in a single mode BIOTAGE® Initiator 2.0 (BIOTAGE®, Uppsala, Sweden).

Microwave-Assisted Synthesis and Characterization of $L_1$ and $L_2$

Figure 1:
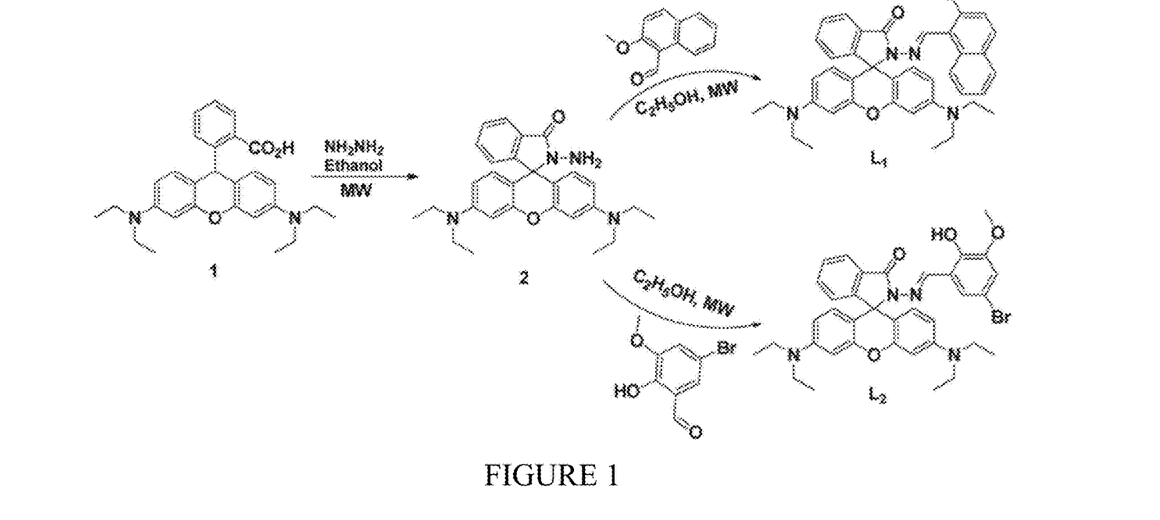
FIG. 1 shows the chemical structures and synthetic routes of $L_1$ and $L_2$.

Sensors $L_1$ and $L_2$ were synthesized from the parent rhodamine B and aromatic aldehydes (2-methoxy-1-naphthaldehyde and 5-bromo-3-methoxy salicylaldehyde) in a two-step Schiff base condensation using MAOS heating protocols, as shown in FIG. 1. Compound 2 was synthesized according to procedure reported in Xiang Y, Tong A, Jin P, Ju Y, Org. Lett 2006, 8, 2863.

Synthesis of Sensor $L_1$

Using microwave heating protocol: A mixture of compound 2 (105 mg, 0.230 mmol), 2-methoxy-1-naphthaldehyde (41 mg, 0.220 mmol) and ethanol (2 ml) was placed in a 10 ml reaction vial. The resulting mixture was stirred to make it homogeneous and it was placed in the cavity of a biotage microwave reactor. The closed reaction vessel was run under pressure and irradiated for 10 min at 100° C. After cooling to room temperature, the resulting solid was filtered and washed three times with cold ethanol. After drying, the sensor $L_1$ was isolated to give in 92% yield. Melting point: 244-246° C.; $^1$H-NMR ($CDCl_3$), δ (ppm): 9.63 (1H, s, N=C—H); 8.77 (1H, t, J=7.4 Hz, H—Ar), 7.74 (1H, d, J=8.4 Hz, H—Ar), 7.71 (1H, d, J=8.0 Hz, H—Ar), 7.63 (1H, d, J=7.7 Hz, H—Ar), 7.48-7.51 (2H, m, H—Ar), 7.15-7.27 (2H, m, H—Ar), 7.12 (1H, d, J=8.4 Hz), 7.09 (1H, d, J=4.9 Hz), 6.63 (2H, d, J=8.8 Hz), 6.44 (2H, d, J=2.2 Hz), 6.28 (2H, dd, J=8.8 Hz, 2.6 Hz), 3.82 (3H, s, $OCH_3$), 3.31 (8H, q, J=6.9 Hz, $NCH_2CH_3$), 1.14 (12H, t, J=6.9 Hz, $NCH_2CH_3$). 13C-NMR ($CDCl_3$), δ (ppm): 164.6, 157.8, 153.4, 151.7, 148.8, 147.6 (N=C—H), 137.6, 133.1, 131.9, 130.3, 129.2, 128.1, 127.0, 126.7, 124.0, 123.2, 116.8, 112.9, 108.1, 107.9, 106.5, 104.6, 79.9, 66.3 (spiro carbon), 56.7, 44.3 ($NCH_2CH_3$), 12.7 ($NCH_2CH_3$); HRMS (ESI): m/z calcd for $C_{40}H_{40}N_4O_3$: 625.3173; Found: 625.3176 [M+H]+.

Synthesis of Sensor $L_2$

Using microwave heating protocol: A mixture of compound 2 (100 mg, 0.220 mmol), 5-bromo-3-methoxy salicylaldehyde (51 mg, 0.221 mmol) and ethanol (2 ml) was placed in a 10 ml reaction vial. The resulting mixture was stirred to make it homogeneous and it was placed in the cavity of a biotage microwave reactor. The closed reaction vessel was run under pressure and irradiated for 10 min at 100° C. After cooling to room temperature, the resulting solid was filtered and washed three times with cold ethanol. After drying, the sensor $L_2$ was isolated to give in 88% yield.

$^1$H-NMR (CDCl$_3$), δ (ppm): 11.11 (1H, s, —OH), 8.94 (1H, s, —CH=N), 7.96 (1H, t, J=6.6 Hz, —Ar), 7.49 (2H, m, —Ar), 6.86 (1H, d, J=6.6 Hz, —Ar), 7.50 (2H, s, —Ar), 6.51-6.43 (4H, m, —Ar), 6.25 (2H, d, J=7.5 Hz, —Ar), 3.82 (3H, s, —OCH$_3$), 3.31 (8H, q, NCH$_2$CH$_3$), 1.16 (12H, t, J=6.6 Hz, NCH$_2$CH$_3$) 13C-NMR (CDCl$_3$), δ (ppm): 163.6, 152.7, 148.5, 146.6 (—CH=N), 138.5, 138.1, 137.7, 134.0, 128.9, 128.5, 127.5, 123.1, 121.8, 121.3, 108.1, 108.0, 106.5, 104.8, 97.3, 80.9, 65.5 (spiro carbon), 56.1, 43.6 (NCH$_2$CH$_3$), 12.4 (NCH$_2$CH$_3$). HRMS (ESI): m/z calcd for C$_{36}$H$_{37}$BrN$_4$O$_4$: 669.2071; Found: 669.2076 [M+H]+.

General Procedure for the Spectroscopic Studies

All spectroscopic measurements were carried out in aqueous CH$_3$CN medium at room temperature. Stock solutions of sensors L$_1$ and L$_2$ (1×10$^{-3}$ M), selected salts of cations (1×10$^{-3}$ M) and anions (1×10$^{-4}$ M) were prepared in CH$_3$CN/H$_2$O. Thus, L$_1$-Al$^{3+}$ and L$_2$-Al$^{3+}$ solutions for N$_3^-$ detection were prepared by addition of 1.0 equivalent of Al$^{3+}$ to the solution of both L$_1$ and L$_2$ (20 μM) in Tris-HCl (10 mM, pH=7.2) buffer containing CH$_3$CN/H$_2$O (7:3, v/v) solution. The resulting solution was shaken well before recording the spectra. Each fluorescence titration was repeated at least thrice until consistent values were obtained. Jobs continuous variation method was used for determining the binding stoichiometry of the complexation reaction. The association constant (K) was calculated from absorbance studies by the linear Benesi-Hildebrand equation. Color changes in solution phase were observed visually under normal light and under a hand-held UV lamp upon addition of various metal ions at room temperature.

Synthesis of Sensors L1 and L2

The synthesis of L$_1$ and L$_2$ were prepared in two steps with 92% and 88% overall yields respectively (FIG. 1). The results obtained indicate that, unlike classical heating, MAOS results in higher yields, shorter reaction time, mild reaction condition, simple work-up procedure and better purity offer privilege over other methods where complex chromatographic techniques are required for purification of the target compounds. The structure of sensors was fully characterized by $^1$H-NMR, $^{13}$C-NMR, FT-IR and HRMS spectroscopy and all data are in accordance with the proposed structure.

Absorption Spectra Studies

Figure 2:
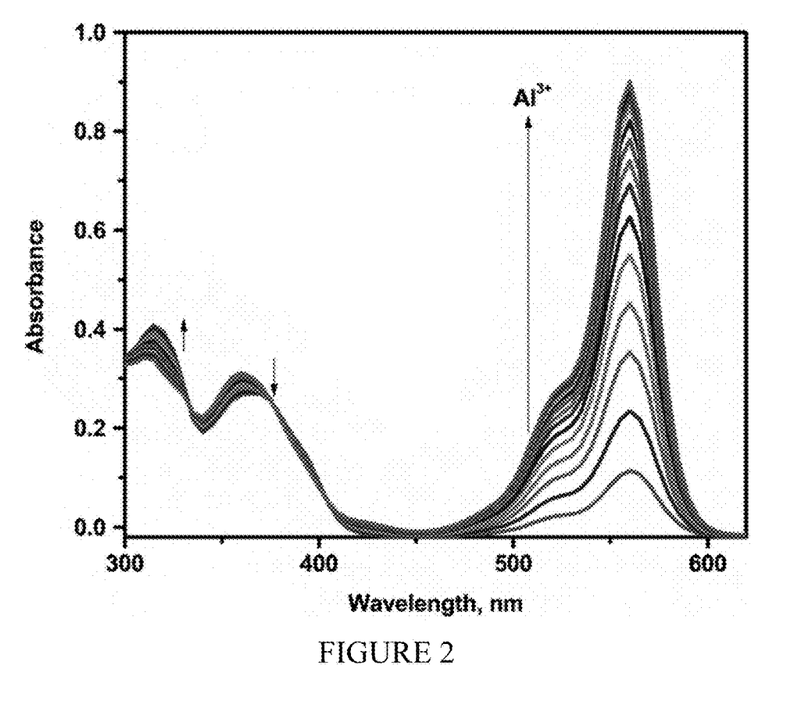
FIG. 2 shows UV-vis spectra of $L_1$ (10 μM) with $Al^{3+}$ (0-23 μM) in $CH_3CN/H_2O$ (7:3 v/v) solution.
Figure 3:
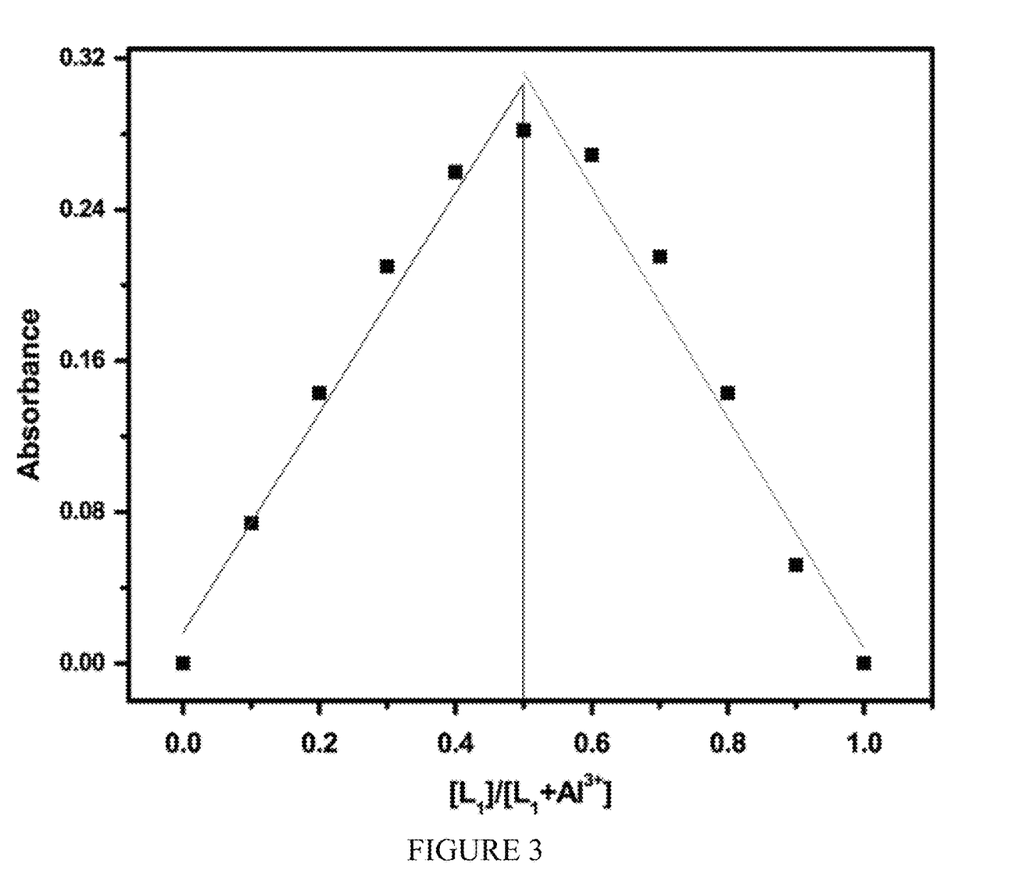
FIG. 3 shows an Absorbance Job's plot for determination of $L_1$-$Al^{3+}$ complex (10 μM) in $CH_3CN/H_2O$ (7:3 v/v) solution.

The metal ion sensing of L$_1$ and L$_2$ were first investigated by UV-vis absorption spectra. The colorless solutions were very weakly fluorescent and showed no absorption above 450 nm, properties which are characteristic of the predominant ring-closed spirolactam. The predominant spirolactam form was further confirmed by observation of the characteristic carbon resonance near 66 ppm for each of the sensors. The UV-vis spectra of sensors were recorded in buffer at 25° C. and showed an absorption maximum at λ=315 nm, which may be attributed to the intramolecular π-π* charge transfer transition. On incremental addition of Al$^{3+}$ ions, the absorption intensity at 315 nm increased gradually and a new absorption peak at 565 nm with a shoulder at 525 nm was generated by ring opening with a visual color change from colorless to pink. The well-defined isosbestic points at 340 and 375 nm clearly indicates the formation of a new complex species between L$_1$ and Al$^{3+}$ ion (FIG. 2). The absorption enhancement is high compared to other metal ions. Selectivity of L$_1$ was checked in the presence of other metal ions. No significant change in the UV-vis spectrum was observed upon the addition of a 10 equivalent excess of other metal ions of interest: Na$^+$, K$^+$, Mg$^{2+}$, Ca$^{2+}$, Ni$^{2+}$, Zn$^{2+}$, Co$^{2+}$, Hg$^{2+}$, Pb$^{2+}$, Fe2+, Fe$^{3+}$, Cr$^{2+}$ and Cu$^{2+}$. Absorption spectra of sensors recorded with the continuous addition of Al$^{3+}$ showed a continuous increase in the absorption at 565 nm and that was employed to calculate binding constants for L$_1$ and L$_2$ with Al$^{3+}$ using the Benesi-Hildebrand method. The plot of absorbance of L$_1$ at 565 nm as a function of mole fraction of added Al$^{3+}$ metal ion reveals that these probes bind to the metal ion in 1:1 stoichiometry (FIG. 3). The complex association constant (K) calculated through the Benesi-Hildebrand equation for Al$^{3+}$ with L$_1$ and L$_2$ were found to be 3.82×104 M$^{-1}$ and 2.41×104 M$^{-1}$, respectively.

Fluorescence Spectral Response of Sensors

Figure 4A:
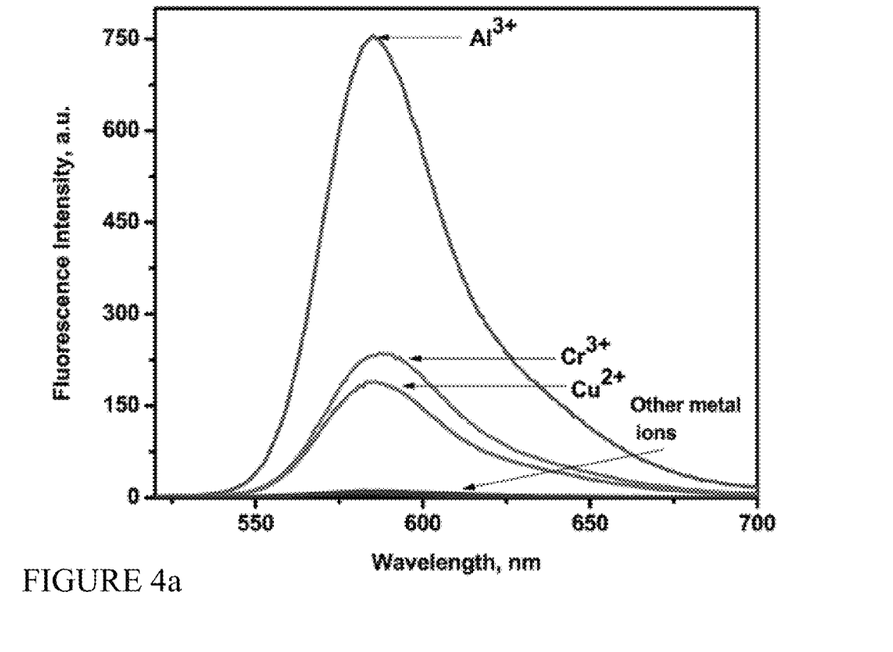
FIG. 4a is a fluorescence spectra of $L_1$ (10 μM) in $CH_3CN/H_2O$ (7:3 v/v) solution ($\lambda_{ex}$=510 nm).
Figure 4B:
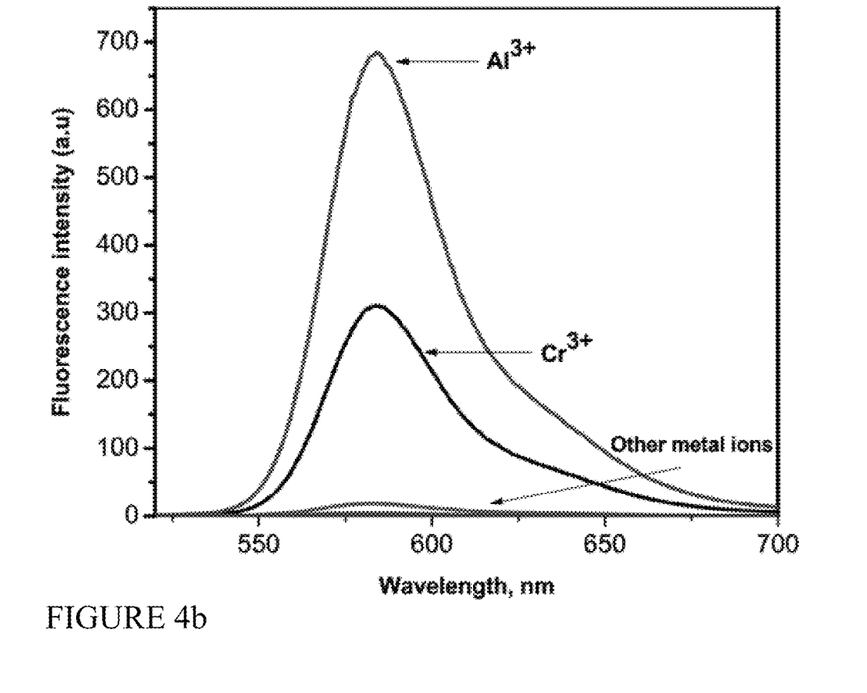
FIG. 4b is a fluorescence spectra of $L_2$ (10 μM) with metal ions (10 μM) in $CH_3CN/H_2O$ (7:3 v/v) solution ($\lambda_{ex}$=510 nm).
Figure 5:
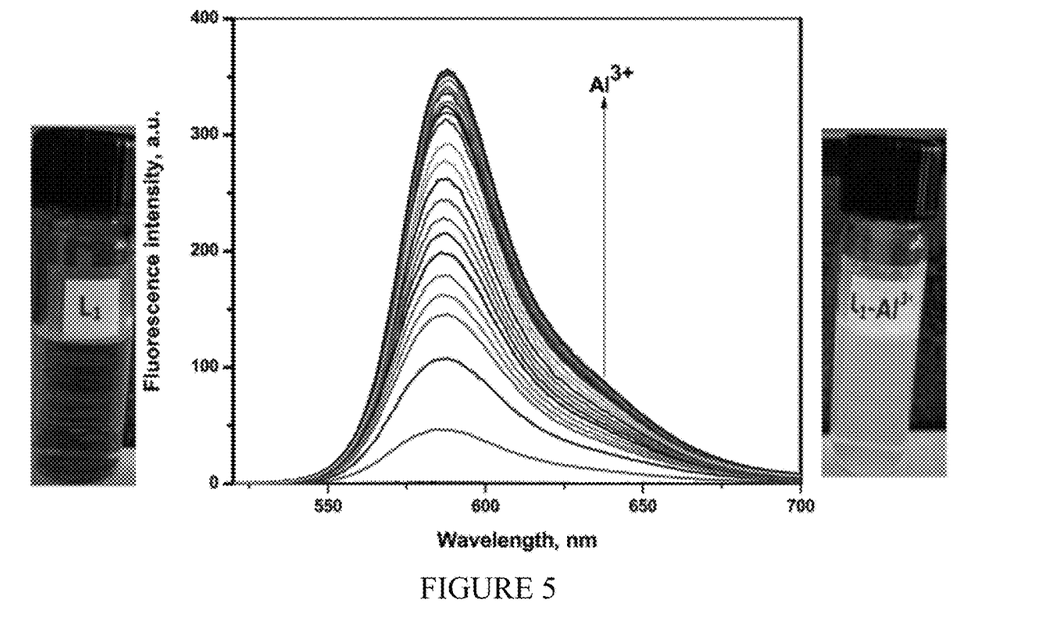
FIG. 5 is a fluorescence spectral titration of $L_1$ (10 μM) on the incremental addition of $Al(NO_3)_3$ (23 equivalents) ($\lambda_{ex}$=510 nm).
Figure 6:
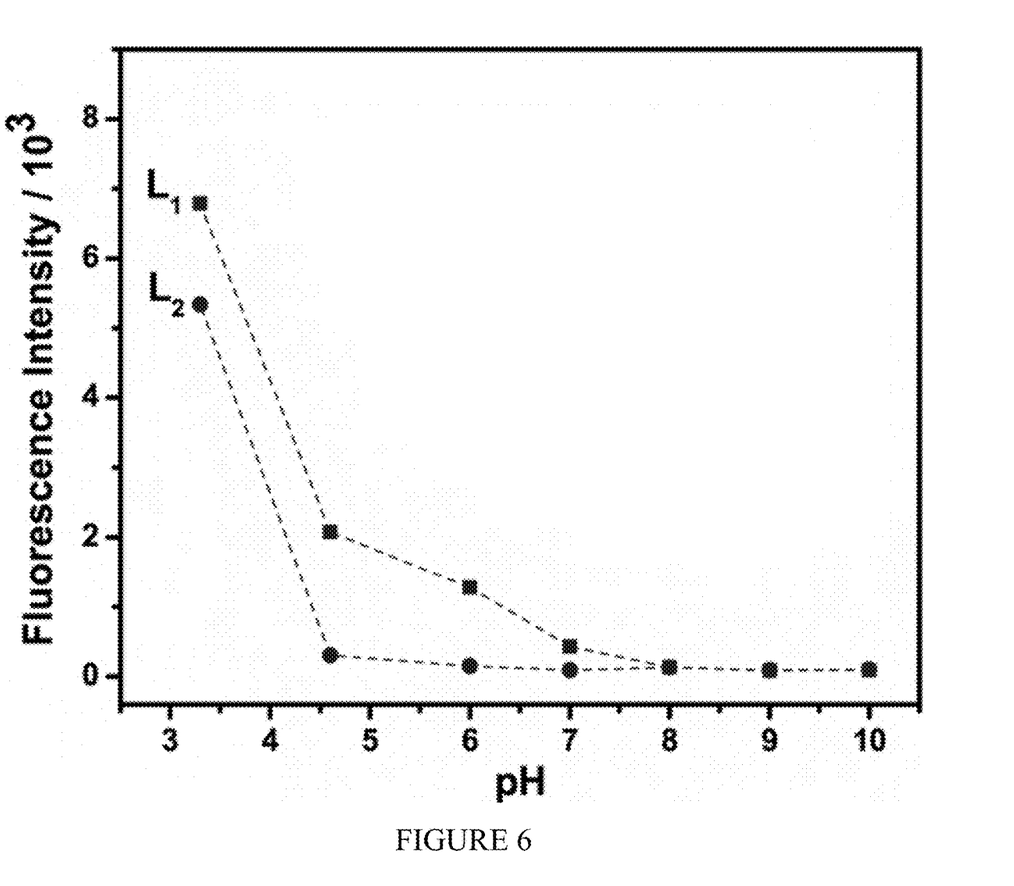
FIG. 6 shows the effect of pH on fluorescence intensity of sensors $L_1$ and $L_2$ (10 μM).

To further explore the sensing behavior of L$_1$ for Al$^{3+}$ ion, the fluorescence spectra of L$_1$ in CH$_3$CN with various metal ions were examined. The fluorescence spectra were obtained by excitation at 510 nm, and both the excitation and emission slit were 5 nm. The fluorescence intensity of L$_1$ upon the additions of metal ions in CH$_3$CN showed a remarkable sensitivity and selectivity towards Al$^{3+}$, even though there were relatively small effects with Cu$^{2+}$ and Cr$^{3+}$ (FIG. 4a). There was a significant emission intensity enhancement with 1.0 equivalent of Al$^{3+}$ which indicates sensor L$_1$ is an excellent turn-on sensor for Al$^{3+}$. This very high fluorescence enhancement is attributed to the formation of ring-open spirolactam in the presence of Al$^{3+}$. This selectivity for Al$^{3+}$ ions over all other ions is due to selective chelate formation with L$_1$ to afford an L$_1$-Al$^{3+}$ complex (See FIG. 7a). When illuminated with a hand-held UV lamp, the addition of Al$^{3+}$ ions to sensor solution resulted in orange fluorescence emission from L$_1$ solution (FIG. 5). The fluorescence profile of L$_2$ were very similar to those for sensor L$_1$: again Al$^{3+}$ registered the highest fluorescence enhancement while other metal ions showed no significant enhancement (FIG. 4b). The fluorescence spectrum of sensors L$_1$ and L$_2$ showed a peak at 585 nm upon the addition of Al$^{3+}$ corresponding to the delocalization in the xanthenes moiety of rhodamine. It is assumed that the spirolactam form was opened upon the addition of Al$^{3+}$ to sensors and makes a highly delocalized π-conjugated stable complexes with Al$^{3+}$ through their active donor sites (e.g., N and O atoms) of receptor part, though other ions failed which basically indicates that the coordinate moiety of L$_1$ and L$_2$ matches perfectly with Al$^{3+}$ ions instead of the other ions. The detection limits of L$_1$ and L$_2$ for Al$^{3+}$ ions were estimated based on the fluorescence titration experiment as 32 μM and 47 μM respectively. Furthermore, the effect of pH values on the fluorescence of L$_1$ and L$_2$ were also investigated in a pH range from 3 to 10. FIG. 6 shows that for free L$_1$ and L$_2$ at pH<5, due to protonation of the open-ring of spirolactam, an obvious color change and fluorescence turn-on appeared. Thus, all the optical measurements were performed in buffer solution with a pH of 7 to keep the sensors in their ring closed form.

Detection of Azide (N$_3^-$)

Figure 7A:
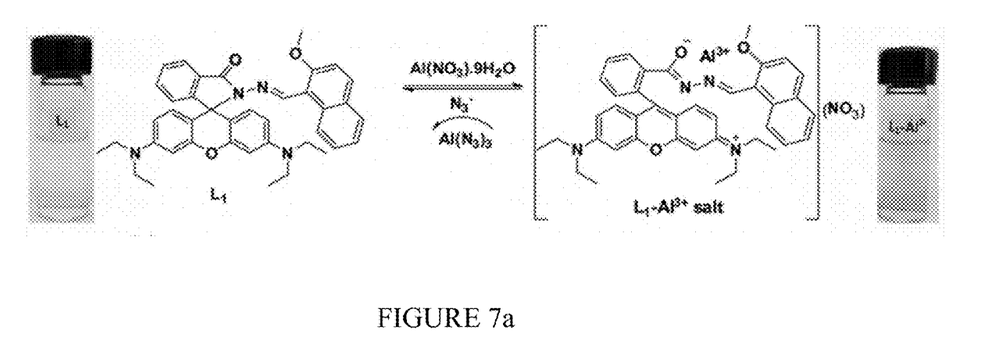
FIG. 7a shows a proposed binding mechanism of sensor $L_1$ towards $Al^{3+}$ in the presence and absence of azide ($N_3^-$).
Figure 7B:
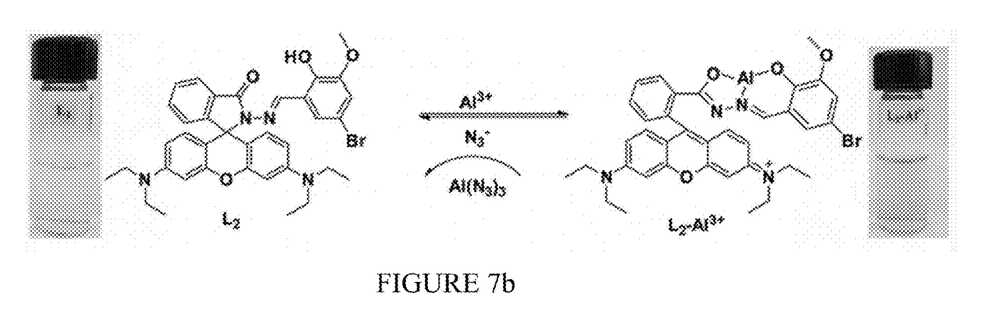
FIG. 7b shows a proposed binding mechanism of sensor $L_2$ towards $Al^{3+}$ in the presence and absence of azide ($N_3^-$).
Figure 8A:
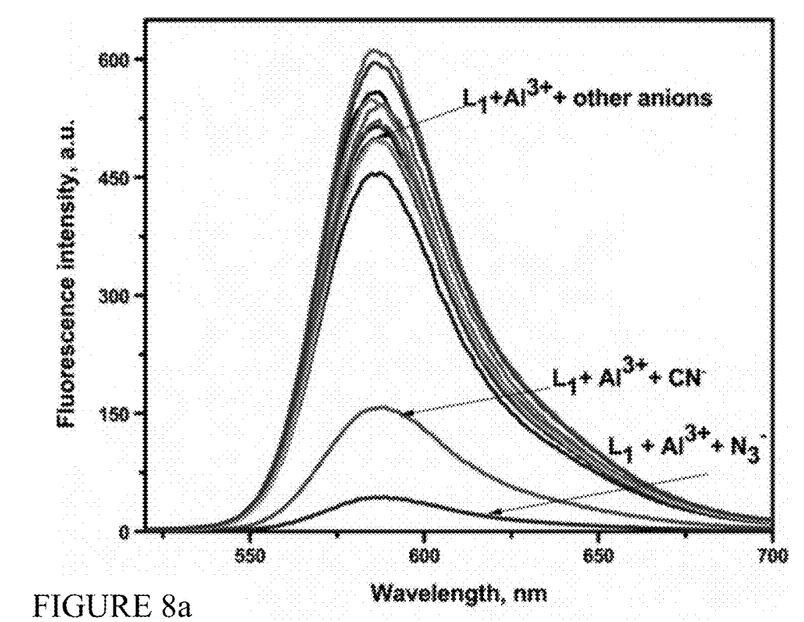
FIG. 8a shows the fluorescence spectra of $L_1$-$Al^{3+}$ (1:1) with anions (10 μM) ($\lambda_{ex}$=510 nm).
Figure 8B:
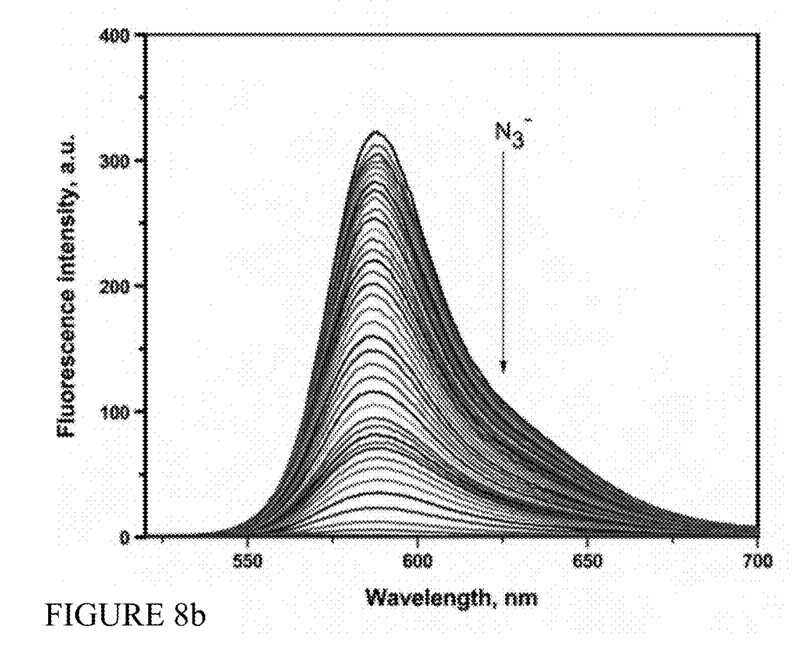
FIG. 8b shows a fluorescence spectral titration of $L_1$-$Al^{3+}$ (23 equivalents of $Al^{3+}$) on the incremental addition of $N_3^-$ (up to 35 equivalents) ($\lambda_{ex}$=510 nm).

Investigation of the reversible binding nature of the sensors is shown in FIG. 8 and FIGS. 7a and 7b. Due to the high stability of AlN$_3$, the L$_1$-Al$^{3+}$ and L$_2$-Al$^{3+}$ complexes serve as a means to detect N$_3^-$. FIG. 8a shows the addition of 20 μM of ancions N$_3^-$, CN$^-$, ClO$_4^-$, CH$_3$COO$^-$, HSO$_4^-$, H$_2$SO$_4^{2-}$, SCN$^-$, Cl$^-$, I$^-$, F$^-$, and OH$^-$ to L$_1$-Al$^{3+}$ (1:1) of which N$_3^-$ alone quenches the fluorescence, with a slight effect for CN$^-$, indicating high selectivity for N$_3^-$. High concentration of CN$^-$ contamination is likely to mislead the fluorescent selectivity of N$_3^-$. So, when L$_1$-Al$^{3+}$ is used as the sensor for N$_3^-$, high concentration of CN$^-$ interference must be eliminated by using mesoporous carbon based adsorbent. The addition of N$_3^-$ to the L$_1$-Al$^{3+}$ solution led to a change in color of the solutions from pink to colorless, which was observed with the naked eye. The addition of $N_3^-$ to the solution containing $L_1$-$Al^{3+}$ complex resulted in the reversal of the $Al^{3+}$ induced changes in the emission band at 585 nm in the fluorescence emission spectra. Gradual addition of $N_3^-$ results in continuous decrease in the emission intensity at 585 nm (FIG. 8b). Based on fluorescence data, the detection limit of $L_1$-$Al^{3+}$ for $N_3^-$ was calculated as 12 µM. A similar finding was observed for complex $L_2$-$Al^{3+}$ towards $N_3^-$ ions. The $L_2$-$Al^{3+}$ system revealed remarkably selective fluorescence "off" behavior exclusively with $N_3^-$. The limit of detection value for $N_3^-$ ions was found at 18 µM. These results show that $L_1$-$Al^{3+}$ and $L_2$-$Al^{3+}$ bind $N_3^-$ ions with higher selectivity and that the process is reversible. The expected binding mechanism of sensors with $Al^{3+}$ in the presence and absence of azide ($N_3^-$) is shown in FIGS. 7a and 7b.

Figure 9:
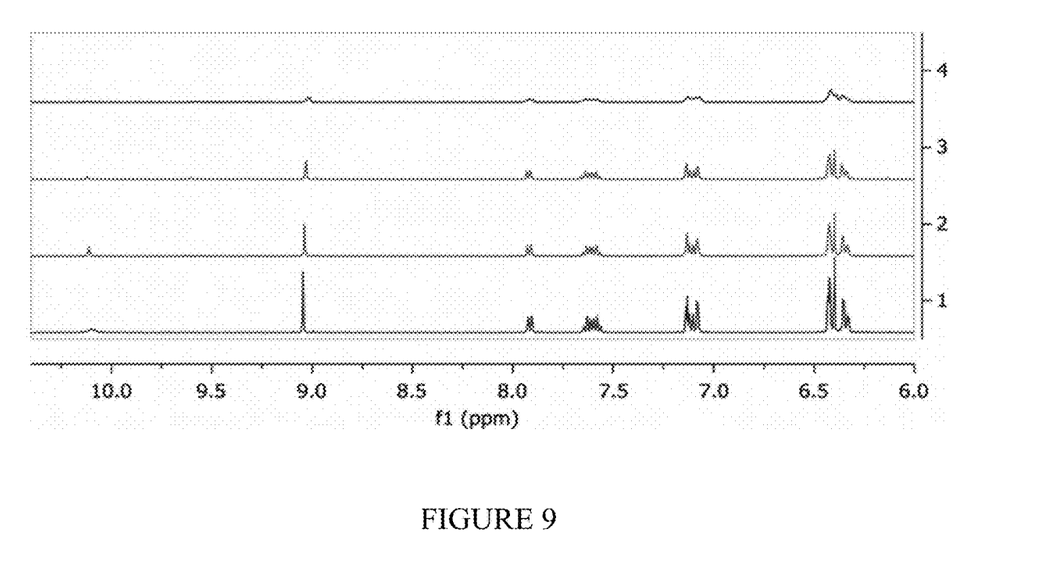
FIG. 9 shows $^1$H-NMR spectral changes of $L_2$ (8 mM) in DMSO-$d_6$ and titrated with 0-1.0 equivalents of $Al^{3+}$ in deuterated water.

FT-IR and $^1$H-NMR Study for Elucidation of Coordination Mechanism Between Sensors and $Al^{3+}$ To elucidate the coordination mechanism of $L_1$-$Al^{3+}$ and $L_2$-$Al^{3+}$ complexes, the FT-IR spectrum of $L_1$ and $L_2$ were conducted in the absence and presence of $Al^{3+}$ ion. The characteristic peak of the amide carbonyl $\gamma_{(C=O)}$ shifted from 1680 cm$^{-1}$ to 1614 cm$^{-1}$ in the presence of $Al^{3+}$, indicating that carbonyl O atoms of the $L_1$ and $L_2$ are involved in the coordination of $Al^{3+}$. $^1$H-NMR was also performed by adding $Al^{3+}$ to deuterated dimethyl sulfoxide (DMSO-d$_6$) solution of $L_2$ as shown in FIG. 9. The $L_2$-$Al^{3+}$ complexes were prepared by the additions of 0.25, 0.5 and 1.0 equivalent $AlCl_3 \cdot 6H_2O$ to the DMSO solution of $L_2$. The peaks observed at δ 10.10 and δ 9.07 are attributable to the phenolic OH and the imine proton (—CH=N—) in $L_2$. Addition of 1 equivalent of $Al^{3+}$ resulted in the disappearance of the hydroxyl proton indicating the binding of $Al^{3+}$ ion through the phenoxide interaction. Further, small unfilled-shifts from 9.07 to 9.00 ppm and shortening of imine protons were observed because of the complex formation between nitrogen atoms and $Al^{3+}$. The formation of the $L_2$-$Al^{3+}$ complex through normal ring opening was confirmed by performing the $^{13}$C-NMR experiment with $L_2$ in the absence and presence of $Al^{3+}$ ions, from which it was observed that the signal at δ=66 ppm attributable to the tertiary carbon of the spirolactam ring in $L_2$ was absent from the spectrum of $L_2$-$Al^{3+}$ complex. Therefore, it is understood that the O atom of phenolic OH, N atom of imine and O atom of spiro ring coordinate to $Al^{3+}$ as shown in FIGS. 7a and 7b.

Geometry Optimization

Figure 10A:
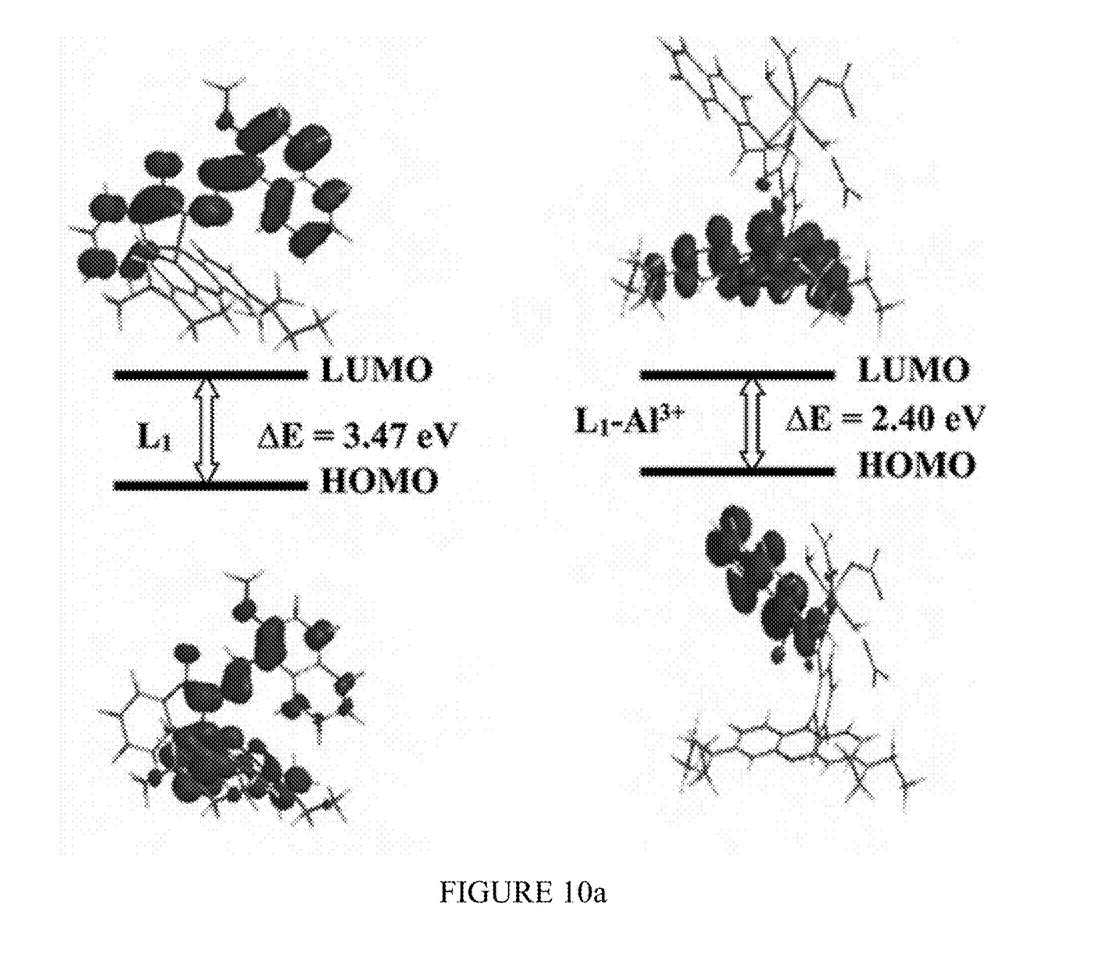
FIG. 10a shows optimized structures and energy correlation of the HOMO-LUMO gap between $L_1$ and $L_1$-$Al^{3+}$ salt.
Figure 10B:
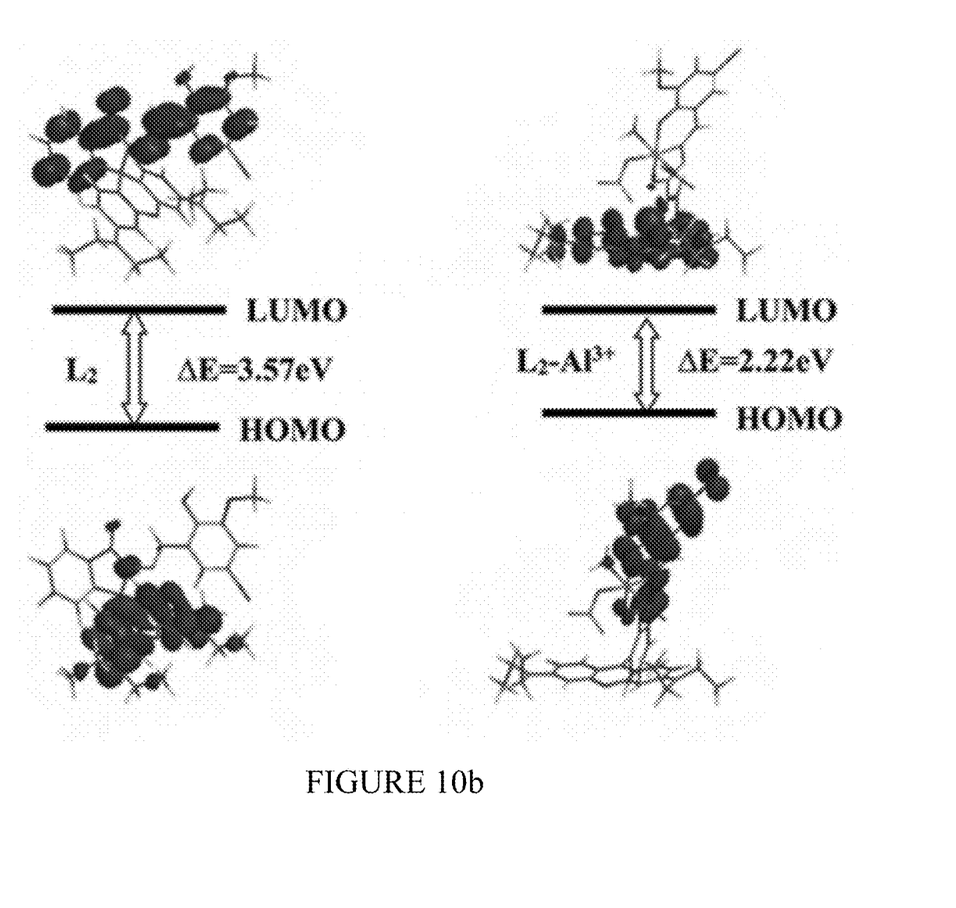
FIG. 10b shows optimized structures and energy correlation of the HOMO-LUMO gap between $L_2$ and $L_2$-$Al^{3+}$ complex.

To better understand the nature of the coordination of $Al^{3+}$ with sensors, theoretical calculations on structures $L_1$, $L_2$, $L_1$-$Al^{3+}$ and $L_2$-$Al^{3+}$ were carried out using Spartan '16 software. Density functional theory (DFT), employing the B3LYP functional and the 6-31G* basis set was used to obtain gas phase, optimized geometries of these structures. The optimized structures of $L_1$, $L_2$ and their respective Al-complexes are depicted in FIG. 10a and 10b. $L_1$ and $L_2$ can undergo rotation of approximately 180° about the N—N bond, producing two prominent cis and trans conformations. For both $L_1$ and $L_2$, the trans conformation is more energetically stable than the respective cis one by approximately 11.3 kJ mol$^{-1}$, owing to anti-arrangement of the methoxy (—OMe) group and the xanthene moiety in trans $L_1$ and to the anti-arrangement of the hydroxyl (—OH) group and the xanthene moiety in trans $L_2$. Additionally, in trans $L_1$ the energy gap between the highest occupied molecular orbital (HOMO) (−4.81 eV) and the lowest unoccupied molecular orbital (LUMO) (−1.34 eV) is 3.47 eV, and in cis $L_1$ the gap, HOMO (−5.03 eV) and LUMO (−1.35 eV), is 3.68 eV. In trans $L_2$, the energy gap, HOMO (−4.86 eV) and LUMO (−1.29 eV) is 3.57 eV, and in cis $L_2$ the energy gap, HOMO (−5.05 eV) and LUMO (−1.22 eV) is 3.83 eV, suggesting that trans $L_1$ and trans $L_2$ are the major equilibrium conformations available stereochemically for direct $Al^{3+}$ coordination. Also, in trans $L_1$, the electron density is delocalized over the entire xanthene moiety with some found on the spirolactam ring as well as on the imine and the ortho-methoxy naphthalene moieties (FIG. 10a). In cis $L_1$, the electron density is mainly localized on half of the xanthene moiety. In both trans $L_2$ and cis $L_2$, the electron density is mainly located over the entire xanthene moiety with some found on the lactam ring nitrogen of both. Moreover, some electron density is also found on the carbonyl oxygen in trans $L_2$ but not on the carbonyl oxygen in cis $L_2$ (FIG. 10b).

Density functional calculations of molecular interactions of trans-$L_1$ and trans-$L_2$ with aqueous aluminum ($Al^{3+}$) nitrate solution revealed that both sensors are energetically stabilized on binding with $Al^{3+}$ ions. For instance, upon formation of $L_1$-$Al^{3+}$ salt complex, the HOMO-LUMO energy gap in trans-$L_1$ (ΔE=3.47 eV) decreased to ΔE=2.40 eV, and upon formation of $L_2$-Al3+ complex, the HOMO-LUMO energy gap in trans-$L_2$ (ΔE=3.57 eV) decreased to 2.22 eV. In $L_1$-$Al^{3+}$ salt complex, formulated as [Al(L$_1$) NO$_3$)$_2$(H$_2$O)$_2$] [NO$_3$], HOMO is primarily delocalized over the methoxy naphthalene moiety, while LUMO is primarily delocalized over the xanthene moiety. In $L_2$-$Al^{3+}$ complex, formulated as Al(L$_2$) (NO$_3$)$_2$(H$_2$O), HOMO is found over the tricyclic structure about $Al^{3+}$ while LUMO is delocalized over the xanthene moiety (FIGS. 10a and 10b).

Vertical electronic excitations of optimized B3LYP/6-31G* trans-$L_1$, trans-$L_2$ and their respective complexes were computed using time-dependent-density functional theory (TD-DFT) Spartan '16 software calculations, formalized in water and using a conductor-like polarizable continuum model (CPCM). In the TD-DFT UV-vis spectrum of trans-$L_1$, an absorption band at λ=379.24 nm with a vertical excitation energy of 3.2693 eV and corresponding to HOMO-2→LUMO excitation (oscillator strength=0.4632) dominates. While in the TD-DFT UV-vis spectrum of trans-$L_1$-$Al^{3+}$ salt complex, an absorption band at λ=422.57 nm dominates, corresponding to HOMO→LUMO excitation (vertical excitation energy=2.9341 eV and oscillator strength=1.0951). In the case of trans-$L_2$, an absorption band at λ=344.32 nm dominates, corresponding to HOMO-2→LUMO excitation with a vertical excitation energy of 3.6008 eV and an oscillator strength=0.3152. For trans-$L_2$-$Al^{3+}$ complex, an absorption band at λ=456.19 nm dominates, corresponding to HOMO-1→LUMO and HOMO→LUMO excitations with a vertical excitation energy of 2.7178 eV and an oscillator strength=0.7824.

CONCLUSION

We have developed reversible fluorescent sensors $L_1$ and $L_2$ for the selective and sensitive sequential detections of $Al^{3+}$ and $N_3^-$ via the fluorescence spectral changes. Upon binding to $Al^{3+}$, obvious detectable change in fluorescence was observed due to the CHEF effect. The in situ prepared $L_1$-$Al^{3+}$ and $L_2$-$Al^{3+}$ complexes were used to detect $N_3^-$ via the metal-displacement approach which displayed an excellent selectivity and sensitivity towards $N_3^-$. Thus, upon the addition of $N_3^-$ to complexes, the intensity of the 585 nm band decreases, indicating release of $L_1$ and $L_2$ from the aluminum complexes. Stoichiometry and binding mechanisms for both sensors are well characterized and established by the respective spectroscopic techniques. These results clearly demonstrate that $L_1$ and $L_2$ sensors described herein will be useful for the analysis of $Al^{3+}$ and $N_3^-$ in environmental samples and biological studies.

The invention claimed is:
1. A compound having the formula:

L₂

2. A compound having the formula:

L₁-Al³⁺

* * * * *